United States Patent [19]

Shaffer et al.

[11] 4,187,243

[45] Feb. 5, 1980

[54] NOVEL 2-(2-CYANOETHYLIDENE)-BICYCLO[2.2.1-]HEPT-5-ENES AND HYDROGENATED DERIVATIVES THEREOF

[75] Inventors: Gary W. Shaffer, Trumbull, Conn.; Kenneth L. Purzycki, Lake Parsippany, N.J.

[73] Assignee: Givaudan Corporation, Clifton, N.J.

[21] Appl. No.: 927,788

[22] Filed: Jul. 25, 1978

Related U.S. Application Data

[62] Division of Ser. No. 860,660, Dec. 15, 1977, Pat. No. 4,132,677.

[51] Int. Cl.$^2$ .................... C07C 121/46; C07C 121/48

[52] U.S. Cl. .................................................... 260/464

[58] Field of Search ......................... 252/522; 260/464

[56] References Cited

U.S. PATENT DOCUMENTS

| | | | |
|---|---|---|---|
| 3,928,247 | 12/1975 | Mookherjee et al. | 260/464 X |
| 4,107,198 | 8/1978 | Myers, Jr. et al. | 260/464 |

OTHER PUBLICATIONS

C.A., 45 (1951), Snyder et al., 5634C.

C. A. 84 (1976), Schroeter, 73726K

*Primary Examiner*—Joseph Paul Brust

*Attorney, Agent, or Firm*—Robert F. Tavares; Thomas Cifelli, Jr.

[57] ABSTRACT

Novel 2-(2-cyanoethylidene)-bicyclo[2.2.1]hept-5-enes and hydrogenated derivatives thereof, their utility as olfactory agents, and perfume compositions containing them.

11 Claims, No Drawings

NOVEL 2-(2-CYANOETHYLIDENE)-BICYCLO[2.2.1]HEPT-5-ENES AND HYDROGENATED DERIVATIVES THEREOF

This is a division of Ser. No. 860,660 filed Dec. 15, 1977; now U.S. Pat. No. 4,132,677 issued Jan. 2, 1977.

SUMMARY OF THE INVENTION

This invention relates to a new class of fragrance compounds having the general formula:

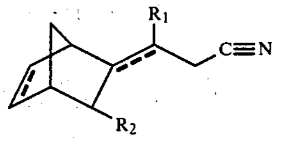

wherein $R_1$ and $R_2$ are alike or different and are chosen from the group consisting of hydrogen or methyl. A dotted line (---) between two carbons indicates that either a double bond or a single bond may exist between those two carbons.

The novel compounds of this invention have spicy, floral odors and are valuable in fragrance compositions. The compounds can be prepared as illustrated below: The symbol ⓐ represents a Knovenagel reaction and ⓑ a hydrogenation.

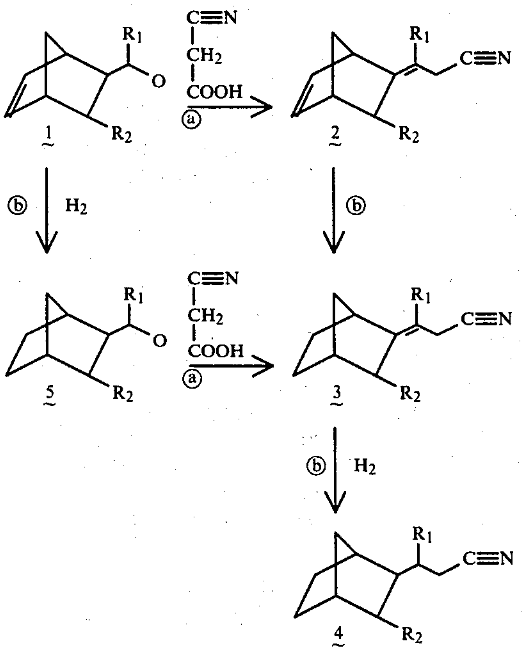

1 2 5 3 4

DESCRIPTION OF PREFERRED EMBODIMENTS

Starting material 1 is a Diels Alder adduct between cyclopentadiene and a suitable dienophile such as acrolein, crotonaldehyde, methyl vinyl ketone, or 3-pentene-2-one.

Compound 1 is then reacted with cyanoacetic acid via the Knovenagel reaction. (See G. Jones, "The Knovenagel Condensation", *Organic Reactions,* R. Adams, et al., Eds., Vol. 15, John Wiley and Sons, Inc., N.Y., 1967 and H. O. House, "Modern Synthetic Reactions", W. A. Benjamin Inc., N.Y. 1965, pp. 225–229). Any of the known variations for preparing $\beta$, $\gamma$ nitriles via the Knovenagel reaction would be suitable for this invention.

The Knovenagel reaction proceeds via an intermediate compound,

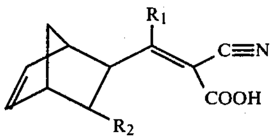

which can be isolated and subsequently thermally decarboxylated. It is preferred, however, not to isolate the intermediate and to decarboxylate the crude reaction mixture. During the latter step the olefinic bond of the side chain shifts into the $\beta$, $\gamma$ position to form 2.

Compound 3 can be prepared by either of the two routes shown. In the preferred method the Diels Alder adduct 1 is hydrogenated to the saturated compound 5. Compound 5 is then reacted with cyanoacetic acid in the Knovenagel reaction to provide compound 3.

Alternatively, the fact that the endocyclic olefin will reduce first allows the conversion of 2 to 3 by catalytic hydrogenation by stopping the reaction after one molar equivalent of hydrogen is absorbed.

Compound 4 can be prepared by catalytic hydrogenation of either 2 or 3 until the required amount of hydrogen has been absorbed.

The compounds of this invention have spice, and floral type odors and are useful in perfume compositions. Such compounds are useful in a variety of odor compositions including rose, jasmin, violet, carnation, galbanum, labdanum, tobacco, leather, cinnamon bark and the like.

It should be noted that in those cases where $R_1$ is methyl, deconjugation taking place during the decarboxylation step can also occur toward the methyl group. Thus, compounds of formulae 3 and 2 wherein $R_1$=methyl are expected to contain some of compound 6.

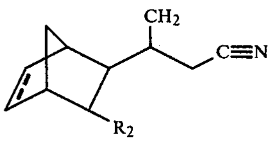

6

Furthermore, under the conditions of the decarboxylation step, i.e., base and heat, it is expected that a proportion of the $\beta$, $\gamma$ double bond in compounds 2 or 3 will shift into conjugation with the cyano group. It is therefore expected that compounds of formulae 2 or 3 will contain small amounts of compounds of formula 7.

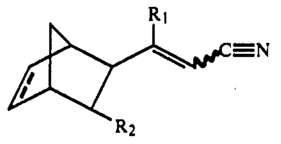

7

It is understood, therefore, that the compounds of this invention having an olefinic bond in the side chain and represented as,

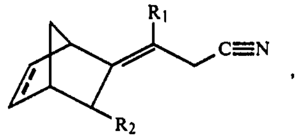

may also be comprised of small amounts of isomers corresponding to 6 and 7. The presence of these isomers is not detrimental to the olfactory properties of the compositions.

While all of the compounds described herein are useful odorants, those of general structure 2 are especially preferred,

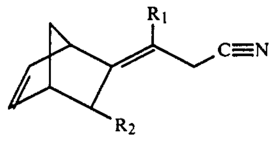

2 their odor being more intense than the corresponding semihydrogenated and hydrogenated compounds.

For the most part the aroma chemicals herein evaluated can be used in perfume formulations in a practical range extending from 0.1 to 30 percent. This will vary, of course, depending upon the type of fragrance formula involved. Higher concentrations above 30 percent (i.e. to 80–90 percent) may be used successfully for special effects.

The compounds can be used to prepare odorant compositions which can be used as odorant bases for the preparation of perfumes and toilet waters by adding the usual alcoholic and aqueous diluents thereto; approximately 15–20% by weight of base would be used for the former and approximately 3–5% by weight would be used for the latter.

Similarly, the base compositions can be used to odorize soaps, detergents, cosmetics, or the like. In these instances a base concentration of from about 0.5 to about 2% by weight can be used.

ILLUSTRATION OF THE PREFERRED EMBODIMENTS

A number of examples are provided herein to illustrate the preferred methods of synthesis of the compounds of this invention and their use as fragrances.

The examples provided herein are intended only to illustrate the preferred embodiments of this invention and should not be construed as limiting. They are intended to embrace any equivalents or obvious extensions which are known or should be known to a person skilled in the art.

Unless otherwise noted infrared spectra were taken as neat samples on a Perkin Elmer 457 spectrophotometer and absorptions are reported as inverse centimeters; nmr spectra were taken on a Varian A-60A spectrometer as chloroform-$d_1$ solutions and are reported as $\gamma$ units relative to TMS; molecular weights were determined with a Perkin-Elmer 270 mass spectrometer. Gas liquid chromatography (glc) was done, on a 2% Carbowax 20M column (18 ft.×⅛ in.).

EXAMPLE I

2-(2-Cyanoethylidene)-3-methylbicyclo[2.2.1]hept-5-ene

A stirred solution of 136 g (1.0 mole) of 2-formyl-3-methylbicyclo[2.2.1]hept-5-ene, 91 g (1.05 mol) of cyanoacetic acid, 3 g (0.05 mol) of ammonium hydroxide (58%), 132 ml of dimethylformamide, and 170 ml of benzene was heated to reflux and the water removed with a Dean-Stark trap. The reaction was allowed to continue until the carbon dioxide evolution ceased (approx. 31 hrs). Upon completion, the reaction was cooled and the solvent removed under reduced pressure. The residual oil was distilled under vacuum to give 120 g (75.5% yield) of 2(2-cyanoethylidene)-3-methylbicyclo[2.2.1]hept-5-ene: b.p. 70°–80° C./1 mm; $n_D^{20}$ 1.5080; ir 3060, 2250, 1460, 1380, 760. 740, 726, 700; nmr 1.15 (3H, d, J=7 Hz, methyl), 4.9–5.5 (1H, m, vinyl H), 5.7–6.1 (2H; m, vinyl H); ms 159.

Anal. Calcd. for $C_{11}H_{13}N$: C, 82.97; H, 8.23; N, 8.80. Found: C, 83.08; H, 8.46; N, 8.82.

EXAMPLE II

2-(2-Cyanoethylidene)-bicyclo[2.2.1]hept-5-ene

A stirred solution of 100 g (0.82 mol) of 2-formyl-5-norbornene (Aldrich Chemical Co.), 65 g (0.76 mol) of cyanoacetic acid, 2 ml of ammonium hydroxide (58%), 132 ml of dimethylformamide, and 170 ml benzene was heated to reflux and the water removed with a Dean-Stark trap. The reaction was allowed to continue until the evolution of carbon dioxide ceased (approx. 24 hrs.). Upon completion, the reaction was cooled and the solvent removed under reduced pressure. The residual oil was distilled under vacuum to give 79.6 g (68% yield) of 2-(2-cyanoethylidene)-bicyclo[2.2.1]hept-5-ene: b.p. 76°–78° C./1 mm; ir 3060, 2260, 1420, 1330, 915, 840, 755, 720; nmr 1.3–2.5 (4H, m), 2.9–3.4 (4H, m), 5.0–5.5 (1H, m), 5.9–6.2 (2H, m); ms 145.

Anal. Calcd. for $C_{10}H_{11}N$: C, 82.72; H, 7.64; N, 9.65. Found: C, 82.77; H, 7.70; N, 9.57.

EXAMPLE III

2-(2-Cyano-1-methylethylidene)-bicyclo[2.2.1]hept-5-ene

A stirred solution of 100 g (0.72 mol) of 2-acetyl-5-norbornene (Aldrich Chemical Co.), 65 g (0.76 mol) of cyanoacetic acid, 2 ml of ammonium hydroxide (58%), 132 ml of dimethylformamide; and 170 ml of benzene was heated to reflux and the water removed with a Dean-Stark trap. The reaction was allowed to continue until the evolution of carbon dioxide ceased (approx. 24 hr.). Upon completion the reaction was cooled and the solvent removed under reduced pressure. The residue oil was distilled under vacuum to give 36 g (31% yield) of 2-(2-cyano-1-methylethylidene)-bicyclo[2.2.1]hept- 5-ene: b.p. 73°–84° C./1 mm; ir 3060, 2255, 2225, 1450, 1420, 1330, 905, 730, 715: nmr 1.2–2.2 (m), 2.7–3.4 (m), 5.0–6.1 (m, vinylic H); ms 159.

Anal. Calcd for $C_{11}H_{13}N$: C, 82.97; H, 8.23; N, 8.80. Found: C, 82.31; H, 8.40; N, 8.78.

EXAMPLE IV 2-(2-Cyanoethylidene)-3-methylbicyclo[2.2.1]heptane

A stirred solution of 97 g (0.7 mol) of 2-formyl-3-methylbicyclo[2.2.1]heptane 65 g (0.76 mol) of cyanoacetic acid, 2 ml of ammonium hydroxide (58%), 132 ml of dimethylformamide, and 170 ml benzene was heated to reflux and the water removed with a Dean-Stark trap. The reaction was allowed to continue until the evolution of carbon dioxide ceased (approx. 24 hrs.). Upon completion, the reaction was cooled and the solvent removed under reduced pressure. The residual oil was distilled under vacuum to give 87 g (77% yield) of 2-(2-cyanoethylidene)-3-methylbicyclo[2.2.1]heptane: b.p. 72°–85° C./1 mm; ir 2940, 2870, 2220, 1610, 1450, 1380, 830, 740; nmr 0.9–1.1 (3H, m), 1.2–2.8 (9H, m), 2.85–3.2 (2H, m), 4.8–5.4 (1H, m); ms 161.

EXAMPLE V 2-(2-Cyanoethylidene)bicyclo[2.2.1]heptane

A stirred solution of 95 g (0.77 mol) of 2-formylbicyclo[2.2.1]heptane, 65 g (0.76 mol) of cyanoacetic acid, 2 ml of ammonium hydroxide (58%), 132 ml of dimethylformamide, and 170 ml benzene was heated to reflux and the water removed with a Dean-Stark trap. The reaction was allowed to continue until the evolution of carbon dioxide ceased (approx. 24 hrs.). Upon completion, the reaction was cooled and the solvent removed under reduced pressure. The residual oil was distilled under vacuum to give 88 g (79% yield) of 2-(2-cyanoethylidene)-bicyclo[2.2.1]heptane: b.p. 72°–80° C./1 mm; ir 2960, 2870, 2260, 1685, 1450, 1420, 1305, 920; nmr 1.15–2.8 (10H, m), 2.96 (2H, m), 4.9–5.4 (1H, m); ms 147.

EXAMPLE VI 2-(2-Cyanoethyl)-3-methylbicyclo[2.2.1]heptane

A mixture of 10.0 g (0.062 mol) of 2-(2-cyanoethylidene)-3-methylbicyclo[2.2.1]heptane, 10 ml of 2B alcohol and 0.1 g of palladium supported on charcoal (5%) catalyst was hydrogenated under 50 psi of hydrogen until 1 equivalent of hydrogen was aborbed. The mixture was then filter, concentrated under reduced vacuum. The residual oil was distilled under vacuum to give 9.6 g (89% yield) of 2-(2-cyanoethyl)-3-methylbicyclo[2.2.1]heptane: b.p. 55°–57° C./0.5 mm; ir 2940, 2870, 2250, 1700, 1460, 1430, 1380; nmr 0.95, 1.1 (3H.5), 1.2–2.5 (14H, m); ms 163.

EXAMPLE VII

Utility of the compounds in perfume bases

The compounds of this invention can be used to provide or enhance spicy notes in perfume compositions.

| A. Carnation type base | pts |
|---|---|
| Aldehyde C-11, 10% in Diethyl Phthalate | 10 |
| Amyl Salicylate | 100 |
| Baccarto ®* | 50 |
| Benzyl Isoeugenol | 30 |
| Cinnamic Alcohol Pure | 75 |
| Cinnamon Leaf Seychelles | 5 |
| Copaiba Oil | 40 |
| Eugenol USP Extra | 50 |
| p-Isopropylcyclohexanol | 100 |
| Isoeugenol | 50 |
| Methyl Isoeugenol | 20 |
| Methyl Undecylenate | 10 |
| 2,6-Dinitro-3-methoxy-4-t-butyltoluene | 15 |
| Nutmeg Oil | 10 |
| Phenyl Ethyl Alcohol | 100 |
| 3,7-Dimethyl-7(6)-octen-1-ol | 200 |
| Trichloromethyl Phenyl Carbinyl Acetate | 30 |
| 7-acety-1,1,4,4-tetramethyl-7-ethyl-1,2,3,4-tetralin | 50 |
| Ylang-Ylang #3 | 50 |
| Compound A | 5 |
| Total | 1,000 |

*Givaudan trademark for a condensation product of citronella oil and acetone.

In the above formulation, compound A represents either the odorless diethylphthalate or a compound of this invention.

When the formulation wherein compound A was 2-(2-cyanoethylidene)-2-methylbicyclo[2.2.1]hept-5-ene was compared to that wherein compound A was diethylphthalate, it was found that the presence of the 2-(2-cyanoethylidene)-2-methylbicyclo[2.2.1]hept-5-ene provided the above composition with intensified spiciness, actually changing the top note from fruity to spicy, and made the total odor impression stronger and more rounded at the same time. The overall effect was of a more natural carnation. The other compounds of this invention may be used in a similar manner. The compounds of general formula 2 are more intense and preferred over those of general formulae 3 and 4.

| B. Detergent Bouquette | Pts |
|---|---|
| The following perfume base was provided: | |
| 2,6-Dintro-3-methoxy-1-methyl-4-t-butylbenzene | 4 |
| β-Naphthyl Methyl Ether | 7 |
| β-Naphthyl Methyl Ketone | 8 |
| 5-t-Butyl-2,4,6-trinitro-meta-xylene | 11 |
| Aldehyde C-8, 10% in Diethyl Phthalate | 3 |
| Aldehyde C-9, 10% in Diethyl Phthalate | 3 |
| Aldehyde C-10, 10% in Diethyl Phthalate | 2 |
| β-Naphthyl Ethyl Ether | 7 |
| Amyl Salicylate Extra | 8 |
| Acetophenone | 4 |
| Benzyl Acetate Prime | 45 |
| Cinnamon Leaf Ceylon Redist. | 50 |
| Citral | 9 |
| Citronella Formosa | 5 |
| Cinnamic Aldehyde | 9 |
| Cedar Leaf Synthetic | 3 |
| Bromostyrol | 3 |
| Cedrenol GD | 13 |
| Neroli 70 | 81 |
| Petitgrain S.A. | 182 |
| Terpinyl Acetate Prime | 135 |
| Lavandin Synthetic AA | 45 |
| Geraniol Standard | 23 |
| Phenyl Ethyl Alcohol Prime | 24 |
| Geranium Bourbon AA Synthetic | 5 |
| Spike Lavender | 30 |
| Resin Styrax White | 7 |
| Patchouli Oil | 5 |
| Lemongrass Native | 51 |
| Orange Oil Terpeneless | 17 |
| Hydroxycitronellal-Methyl Anthranilate Schiff Base | 11 |
| Methyl Benzoate | 23 |
| Dimethyl Benzyl Carbinyl Acetate | 5 |
| Benzyl Alcohol | 44 |
| Linalool | 12 |
| Linalyl Acetate | 33 |
| Phenyl Propyl Aldehyde | 1 |
| Mellitis #3 Synthetic ®* | 5 |
| Resin Oakmoss Soluble | 1 |

-continued

| B. Detergent Bouquette | Pts |
|---|---|
| Terpineol | 65 |
| Resin Labdanum Absolute, 50% in Diethyl Phthalate | 1 |
| Total | 1,000 |

*Trademark of Givaudan Corporation, for a liquid perfume base used in finished perfumes, colognes, cosmetics and soaps.

The addition of 2-(2-cyanoethylidene)-2-methylbicyclo[2.2.1]hept-5-ene produces a blending of the aldehydes present in this perfume oil and makes the whole composition more uniform while retaining the floral quality. Levels of 0.1%-1.0% wt. can be used, and 1.0% appears to give optimum effect. Higher amounts can be used for different and special effects.

The other compounds of this invention may be used in a similar manner.

We claim:

1. A compound of the general formula:

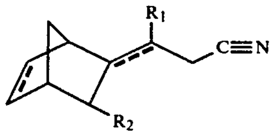

wherein: $R_1$ and $R_2$ may be alike or different and are chosen from the group consisting of hydrogen or methyl and the dotted line between two carbons indicates that the carbons are connected by either a single or a double bond.

2. A compound according to claim 1 wherein the general formula is:

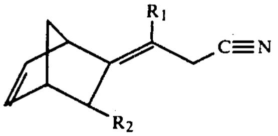

3. A compound of claim 2 wherein $R_1$ and $R_2$ are both hydrogen.

4. A compound of claim 2 wherein $R_1$ is hydrogen and $R_2$ is methyl.

5. A compound of claim 2 wherein $R_1$ is methyl and $R_2$ is hydrogen.

6. A compound according to claim 1 wherein the general, formula is:

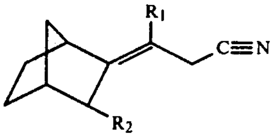

7. A compound according to claim 6 wherein $R_1$ and $R_2$ are both hydrogen.

8. A compound according to claim 6 wherein $R_1$ is hydrogen and $R_2$ is methyl.

9. A compound according to claim 1 wherein the general formula is:

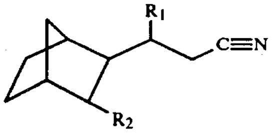

10. A compound of claim 9 wherein $R_1$ and $R_2$ are hydrogen.

11. A compound of claim 9 wherein $R_1$ is hydrogen and $R_2$ is methyl.

* * * * *